United States Patent [19]

Hayat

[11] 4,344,202
[45] Aug. 17, 1982

[54] ELECTRIC TOOTHBRUSH

[76] Inventor: Victor Hayat, 169 Bd Malesherbes, 75017 Paris, France

[21] Appl. No.: 119,011

[22] Filed: Feb. 6, 1980

[30] Foreign Application Priority Data

Feb. 22, 1979 [FR] France .............................. 79 04512

[51] Int. Cl.$^3$ ............................................. A46B 13/02
[52] U.S. Cl. ........................................ 15/4; 15/22 R; 15/23
[58] Field of Search ............................ 15/22, 23, 24, 4; 128/62 A

[56] References Cited

U.S. PATENT DOCUMENTS

| | | | |
|---|---|---|---|
| 1,795,098 | 3/1931 | Scadding | 15/23 |
| 2,134,934 | 11/1938 | Wilhoit | 15/23 |
| 2,840,837 | 7/1958 | Gustems | 15/23 |
| 3,551,932 | 1/1971 | Grossman | 15/23 |

Primary Examiner—Chris K. Moore

[57] ABSTRACT

This electric toothbrush is of the type in which the brush is rotated about its longitudinal shaft; this shaft is extended forwards by a tip able to be introduced into the interdental space for massaging the papilla and cleaning the mesial and distal faces of the teeth; the brush is enveloped over about a third of its periphery by a coaxial gutter and this coaxial gutter terminates in a raised fork-shaped end which serves as a free guide for the end of the longitudinal shaft of the brush; the rotational movement of this shaft imparts thereto a simultaneous reciprocal movement which is transmitted to its tip.

4 Claims, 5 Drawing Figures

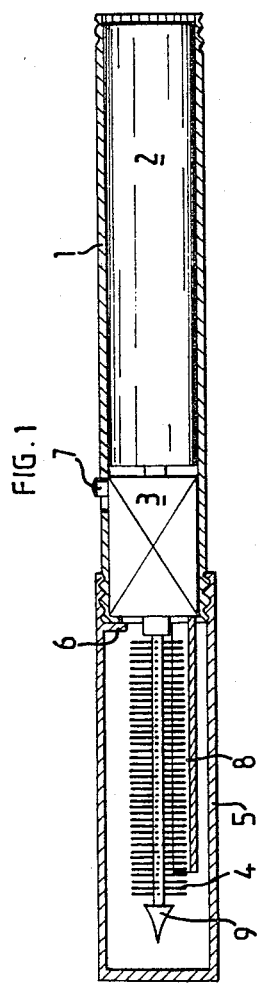
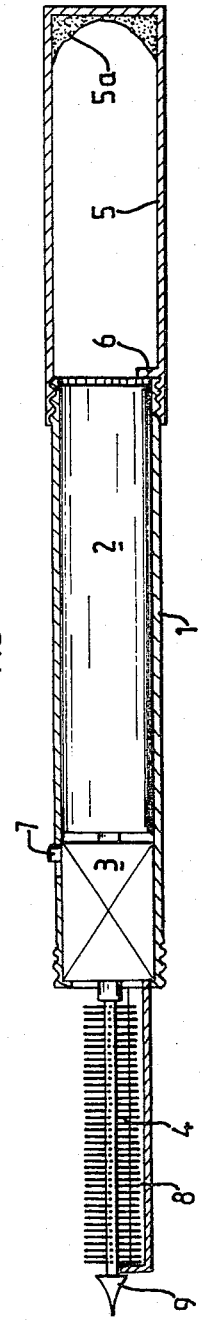
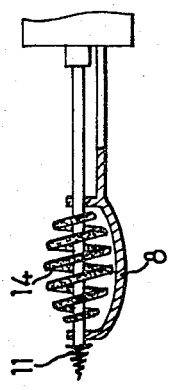
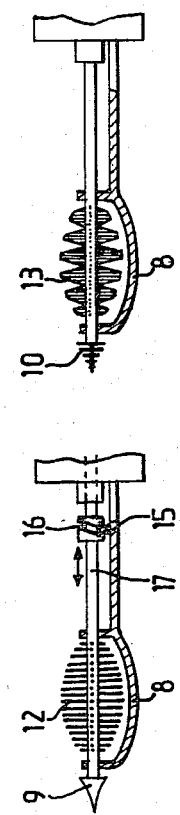
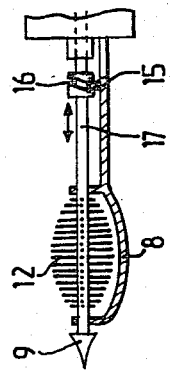

ELECTRIC TOOTHBRUSH

BACKGROUND OF THE INVENTION

Some electric toothbrushes known at present comprise a brush similar to those for hand toothbrushes but generally smaller in size than the ones most usually used, to which a small electric motor supplied by battery, accumulator or power plug, imparts an oscillating, jerky, generally reciprocal movement which is more or less complicated.

The brush may also be rotated continuously about a longitudinal axis to avoid contact between the brush and the tissues which have no need to be brushed (cheeks, tongue, palate . . . ), this brush being often surrounded, over about a third of its periphery, by a coaxial gutter.

SUMMARY OF THE INVENTION

The present invention provides an electric toothbrush whose brush is rotated continuously about its longitudinal shaft, and wherein the longitudinal shaft of the brush is extended by a tip able to be introduced into the interdental space for massaging the papilla and for cleaning the mesial and distal faces of the teeth.

A slight reciprocating movement small in amplitude may be imparted to the brush in certain cases of paradontopathology in order to remove more completely the dental plaque, which is an essential casual agent in diseases of the teeth and of the periodontal tissue; this reciprocating movement of the brush may be communicated thereto by any appropriate means, particularly by means of a transverse fixed pin engaged in an appropriate shaped groove integrally formed in the shaft of the brush, or by means of a transverse pin integral with the shaft engaged in an appropriately shaped inner groove of a fixed coaxial cylinder.

According to another feature of the invention, the brush is partially surrounded by a protecting gutter, in a way known per se, and this coaxial gutter terminates in a raised fork-shaped end which serves as a free guide for the end of the longitudinal shaft of the brush.

The above and other objects, features and advantages of the present invention will become apparent from the following description given solely by way of non-limiting illustration, when taken in conjunction with the accompanying drawings.

DESCRIPTION OF THE DRAWINGS

The drawings show schematically by way of example one embodiment of the present invention.

FIG. 1 is a sectional view of the brush at rest.

FIG. 2 is a similar view, but with slight variations, of the brush ready to be used.

FIGS. 3 to 5 are partial views showing variations.

DESCRIPTION OF THE PREFERRED EMBODIMENT

The brush shown comprises a cylindrical handle 1, inside which are housed at least one battery 2 and a rotary motor 3, with its output shaft capable of rotating the cylindrical brush 4; a screwed cap 5 protects brush 4. When the cap is unscrewed from the front part of the brush, as shown in FIG. 1, and is screwed to its rear part, as shown in FIG. 2, its pin 6 provides connection between battery 2 and reversing switch 7.

The cap shown in FIG. 2 comprises at its bottom a cavity for housing a material 5a absorbing humidity, or impregnated with an antiseptic liquid or similar, or a possibly volatile fragrant tablet, or a paste.

This reversing switch 7, within reach of the fingers of the user, allows contact to be made and the direction of the current in motor 3 to be reversed and, consequently, the direction of rotation of brush 4.

A gutter 8, concentric with brush 4 and disposed in the vicinity thereof, envelops it over about a third of its periphery, and prevents contact between the brush and the buccal tissues which do not need to be brushed (cheeks, tongue, palate . . . ); this gutter may terminate in a raised fork-shaped end which serves as a free guide for the end of the rod of the brush, as shown in FIG. 2.

The shaft of the brush is extended by a tip 9 which may be made from wood or a plastic, natural, artificial or synthetic material; it may also be provided with tufts of bristles 10, whose length decreases preferably towards the front, as shown in FIG. 4, or in a spiral 11, as shown in FIG. 5.

The brush, with or without the gutter, could be removable and changeable instead of being fixed; its shape could be any other than cylindrical, and particularly cylindro-conical; a simple mechanical device could be used for combining with its rotary movement about its axis a reciprocal movement parallel thereto and possibly even perpendicular thereto; seals may be provided for sealing the cylindrical sleeve containing the battery and the motor; the cap, instead of being screwed on, may be secured in any other way.

Thus, FIGS. 3 to 5 show three brushes in which the brush is much shorter, and is formed either by uniformly distributed bristles 12 or tufts of bristles 13 longer in the centre than at the ends, or bristles mounted in a spiral 14.

A low amplitude reciprocating movement may be imparted to brush 4, or 12 to 14, and to the tip 9 to 11, by means of a transverse pin 15 engaged in an appropriately shaped groove 16 provided on the periphery of shaft 17 of the brush, as shown in FIG. 3.

It is apparent that within the scope of the invention, modifications and different arrangements can be made other than are here disclosed. The present disclosure is merely illustrative with the invention comprehending all variations thereof.

What is claimed is:

1. An electric toothbrush comprising a rotatable brush, a shaft mounting said brush, means for rotating said brush continuously about its longitudinal axis, means for conferring a reciprocal movement to said brush, and a tip mounted at the end of the shaft of said brush, said tip being conical in shape with a sharply pointed apex and an apex angle sized to permit said tip to be introduced into and through the interdental space for massaging the papilla and cleaning the mesial and distal faces of the teeth.

2. An electric toothbrush according to claim 1, wherein the brush is surrounded over about a third of its periphery by a co-axial gutter which terminates in an end in the form of a raised fork which serves as a free guide for the tip.

3. An electric toothbrush according to claim 2, wherein said tip has radial tufts of bristles of a length decreasing in the forward direction.

4. An electric toothbrush according to claim 3, wherein said bristles are in the form of a spiral.

* * * * *